Figure 1:
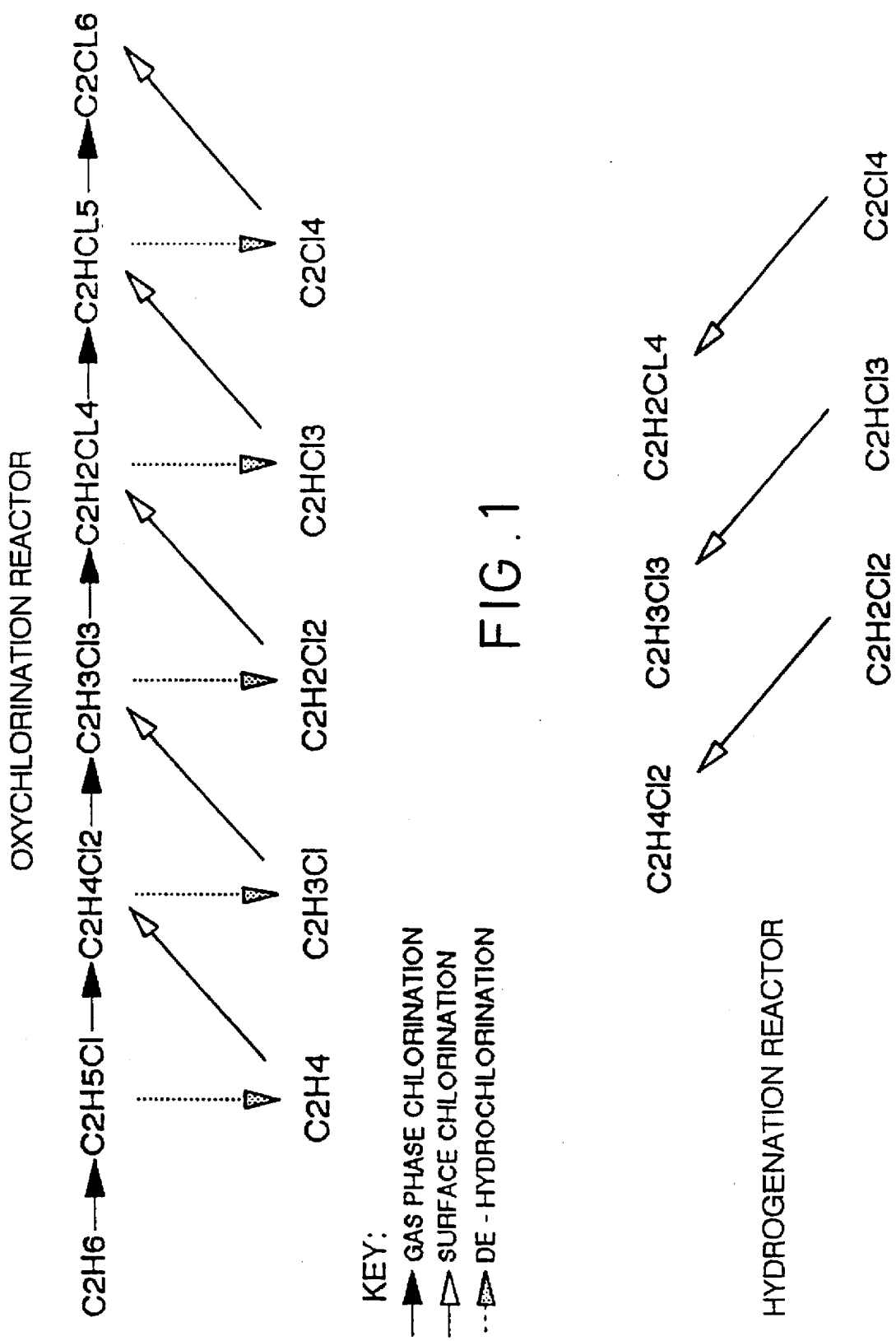

United States Patent [19]
Clegg et al.

[11] Patent Number: 5,763,710
[45] Date of Patent: Jun. 9, 1998

[54] OXYCHLORINATION PROCESS

[75] Inventors: Ian Michael Clegg, Middlewich; Ray Hardman, Chester, both of United Kingdom

[73] Assignee: EVC Technology AG, Zug, Switzerland

[21] Appl. No.: 797,841

[22] Filed: Feb. 10, 1997

Related U.S. Application Data

[63] Continuation of Ser. No. 433,383, filed as PCT/GB94/01942 published as WO95/07249, abandoned.

[30] Foreign Application Priority Data

Sep. 7, 1993 [GB] United Kingdom ............... 9318497

[51] Int. Cl.$^6$ ............................................ C07C 17/15
[52] U.S. Cl. ............................................ 570/224; 570/222
[58] Field of Search ........................................ 570/222, 224

[56] References Cited

U.S. PATENT DOCUMENTS

| | | |
|---|---|---|
| 3,879,481 | 4/1975 | Sze et al. . |
| 3,937,744 | 2/1976 | Riegel . |
| 3,987,118 | 10/1976 | Kuck . |
| 4,124,534 | 11/1978 | Leitert . |
| 4,300,005 | 11/1981 | Li . |
| 4,451,683 | 5/1984 | Davies . |
| 5,113,227 | 5/1992 | Mainz . |
| 5,260,247 | 11/1993 | Helmut . |

FOREIGN PATENT DOCUMENTS

| | | |
|---|---|---|
| 2285359 | 4/1976 | France . |
| 567714 | 12/1977 | U.S.S.R. . |
| 1256245 | 12/1971 | United Kingdom . |
| 1492945 | 11/1977 | United Kingdom . |
| 2009164 | 6/1979 | United Kingdom . |
| 2101596 | 1/1983 | United Kingdom . |

*Primary Examiner*—Alan Siegel
*Attorney, Agent, or Firm*—Woodcock Washburn Kurtz Mackiewicz & Norris LLP

[57] ABSTRACT

A method for the catalytic oxychlorination of ethane to VCM comprising combining ethane and a chlorine source in an oxychlorination reactor in the presence of an oxychlorination catalyst, the reaction conditions being selected to reduce the influence of the oxychloride form of the catalyst, separating the VCM product from the output of the reactor and recycling the by-products to the reactor.

11 Claims, 1 Drawing Sheet

OXYCHLORINATION PROCESS

This is a continuation of U.S. application Ser. No. 08/433,383, filed Aug. 15, 1995, now abandoned which is a 371 of PCT/GB94/01982 filed Sep. 7, 1994.

The present invention relates to a process for the catalytic production of vinyl chloride monomer (VCM) from ethane via oxychlorination of ethane.

Most commercial processes for the production of VCM utilise ethylene and chlorine as the raw materials. Ethylene is in general chlorinated by contact with chlorine and a catalyst in liquid 1,2-dichloroethane. The dichloroethane is subsequently dehydrochlorinated at an elevated temperature to yield VCM and hydrogen chloride.

The use of ethylene as a starting material is a significant factor in the cost of producing VCM. In general, significant reductions in this cost can only be achieved by economies of scale since established processes are operating at close to maximum efficiency.

A further disadvantage of the use of ethylene is that the dehydrochlorination of the 1,2-dichloroethane intermediate yields hydrogen chloride. Disposal thereof is usually achieved by catalytic oxychlorination with ethylene in a further processing step to yield more 1,2-dichloroethane.

An alternative, known method for the production of VCM involves the use of ethane. The use of alternative hydrocarbon raw materials, of which ethane is the primary candidate, immediately addresses the issue of the cost of ethylene by substituting it with a cheaper alternative. Additionally, the chemistry of VCM production using alternative hydrocarbons may hold advantages. For example, VCM production can be achieved in a single step.

Three chemical approaches are known for the conversion of ethane to VCM. These are gas phase chlorination, catalysed oxidation of oxychlorination. Of these, a process based on oxychlorination is the most attractive:

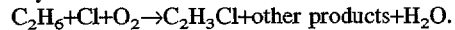

$C_2H_6 + Cl + O_2 \rightarrow C_2H_3Cl + \text{other products} + H_2O$.

The chlorine source may be $Cl_2$, HCl or a chlorinated hydrocarbon. Where HCl is the source, the opportunity arises to utilise one of the intermediate products of VCM production from ethylene.

The production of VCM from ethane has not enjoyed commercial success. A number of attempts have been made, but the processes used have suffered from a number of drawbacks which, while inconvenient in a laboratory, become unacceptable when the process is applied on an industrial scale.

A number of catalysts have been proposed for the catalytic oxychlorination of ethane.

The most promising catalysts appear to be fluidised bed catalysts based on copper. GB 1492945 (BP) describes such a catalyst, consisting of copper, potassium and cesium chlorides evaporated onto an alumina support, together with a cerium chloride component. However, it is not apparent that the precise formulation used by BP was successful, because the ethane feed used is diluted with in excess of 50% nitrogen gas, impractical in industrial applications, and comprehensive results are not reported. Most by-products of the oxychlorination reaction are ignored. Furthermore, elevated temperatures (530° C.) were employed.

SU 567714 also discloses a copper/potassium catalyst for the oxychlorination of ethane. However, the particular formulation used is only disclosed to be effective above 550° C., and up to 62.4% of the ethane reacted is unaccounted for in the quoted product spectrum.

GB 2009164 (Monsanto) describes, among others, a copper/potassium catalyst. However, the precise formulation used does not appear to be effective below 500° C. Furthermore, the quoted results are uninformative since it would appear that ethylene generation has been either ignored or confused with VCM generation. The % conversion to VCM is not given.

From the above-cited art, it is evident that the selectivity of the oxychlorination reaction to VCM is not complete. This remains a largely inconsidered source of inefficiency in the oxychlorination process.

An appreciable percentage of the by-products of the oxychlorination reaction is comprised by combustion products, which are generated by oxidation of hydrocarbons such as ethane to form, mainly, $CO_2$. These products represent a wastage of raw materials. However, they are essentially ignored in the prior art. No attempt to reduce the production of these by-products has been made except through catalyst formulations, which, as evidenced by the above-cited art, has its limitations.

A further source of inefficiency in the oxychlorination of ethane is due to the production of by-products other than combustion products. Such by-products are largely chlorinated hydrocarbons and, in some cases, are capable of being converted to VCM. However, these by-products are also ignored in the prior art.

For example, in GB 1256245 (Princeton Chemical Research, Inc.) "other chlorinated materials" are produced at a level of about one tenth of the yield of vinyl chloride. There is no suggestion in GB 1256245 as to how such by-products should be dealt with. However, it can be seen that they constitute an appreciable fraction of the total yield of the reaction.

U.S. Pat. No. 3,879,481 (Lummus Co.) acknowledges the production of chlorinated by-products in the form of chlorinated hydrocarbons, such as trichloroethane, trichloroethylene, tetrachloroethane and the like. It is suggested that these by-products be burned, resulting in the loss of their feedstock value. Even if the hydrogen chloride produced is recovered, the carbon content of the by-products is lost.

It has now been found that it is possible to significantly increase the efficiency of the oxychlorination reaction by addressing the problems heretofore ignored.

In a first aspect of the present invention, there is provided a method for the catalytic oxychlorination of ethane to VCM comprising combining ethane and a chlorine source in an oxychlorination reactor in the presence of an oxychlorination catalyst, the reaction conditions being selected to reduce the influence of the oxychloride form of the catalyst, separating the VCM product from the output of the reactor and recycling the by-products to the reactor.

The generation of combustion products in the oxychlorination process is promoted by the oxychloride form of the catalyst. It has been found that selecting reaction conditions to reduce the concentration of this form, and therefore its influence, reduces the quantity of combustion products generated in the reaction.

The influence of the oxychloride form of the catalyst may be reduced, for example, by increasing the temperature of the reaction. However, this solution has disadvantages in that, for example, a greater amount of energy will be required to heat the reactor, leading to increased production costs.

Preferably, the influence of the oxychloride form of the catalyst is reduced by promoting its rapid reaction with a reactant.

It has been found that certain sources of chlorine react very rapidly with the oxychloride form of the catalyst, consequently reducing the amount of combustion products formed in the reaction. Preferably, therefore, the influence of the oxychloride form of the catalyst is reduced by supplying an appropriate chlorine source in excess of the stoichiometric requirement for chlorine.

Preferably, the chlorine source comprises HCl.

The HCl may be the only source of chlorine in the oxychlorination reaction. Alternatively, it may be supplied together with a second chlorine source, such as a chlorinated hydrocarbon or chlorine itself. All the chlorine requirement may be supplied by the second chlorine source.

In general, the greater the excess of HCl supplied over its stoichiometric requirement the greater the beneficial effect on the selectivity of the oxychlorination reaction. Where there is no requirement for HCl, because all the chlorine requirement is supplied in an alternative form, any quantity of HCl which is added will have a beneficial effect.

The ratio of HCl to ethane used in the reaction is preferably in the range 0.1 to 10 on a molar basis, and advantageously in the range 0.5 to 3.

Because not all the HCl is consumed in the reaction, HCl will leave the reactor together with the products of the reaction. Preferably, the excess HCl is recycled to the reactor.

Recovery of the HCl in order to recycle it may be accomplished by any conventional means known in the art.

Reactors and means for combining ethane and a chlorine source are well known in the art. For example, reaction conditions are described in the prior art referenced above.

Preferably, however, the catalyst comprises a copper salt and an alkali metal salt deposited on an inert support. Preferably, the copper and the alkali metal are present in the atomic ratio of 2:8.

The alkali metal may be lithium, potassium, sodium or rubidium. Preferably, however, the alkali metal is potassium.

The atomic ratio of the copper and potassium constituents quoted correspond to the weight percentages of 1.3% and 3.4%.

Preferably, a lanthanide salt may be used as an additional constituent. The preferred lanthanide is cerium, which may be added in atomic ratio between 0.1 and 5. Advantageously, a weight percentage of 0.74% of cerium is used, equivalent to an atomic ratio of 0.5.

Alternatively, an alkali earth metal may be used as an additional component. Preferred alkali earth metals are magnesium and calcium.

The inert carrier for the catalyst may be chosen from a number of supports known in the art which are readily available. For example, such supports include alumina, silica gel, silica-alumina, silica-magnesia, bauxite, magnesia, silicon carbide, titania, zirconium silicate and the like.

Preferably, the support is alumina. The preferred alumina is one having a low surface area to weight ratio. Preferably, this ratio is below 5 $m^2/g$ and advantageously it is around 1 $m^2/g$.

The catalyst may be used in a fixed bed or fluidised bed mode. Preferably, a fluidised bed is used. Fluidisation is accomplished by breaking up the catalyst into particles, which advantageously have a mean particle size of about 90 microns.

The metal salts used in the catalyst are preferably metal chlorides. However, nitrates, carbonates and hydroxides may be used, which will be converted to chlorides, oxides or oxychlorides under reaction conditions.

The ethane feed used in the oxychlorination reaction may be of high purity, or may contain appreciable quantities of other hydrocarbons such as ethylene or methane, as in commercial or technical grade ethane supplies.

Oxygen may be supplied in the form of $O_2$ gas, or oxygen enriched air may be used.

Chlorine is provided in the form of $Cl_2$ gas, HCl or a chlorinated hydrocarbon, or mixtures thereof.

The ratios in which the various components of the reaction are advantageously mixed may be determined empirically. The preferred ratio for ethane to oxygen, however, is 1:0.25 to 1:1.4, and advantageously 1:0.75 to 1:1. The ratio of ethane to chlorine is preferably 1:0.5 to 1:5. All ratios are expressed on a molar basis.

The catalyst of the invention may be operated between the temperatures of 400° and 550° C. Preferably, however, the operating temperature is between 440° and 500° C. and more preferably it is between 450° and 470° C.

The catalyst may be operated at a pressure in the range 0 to 30 BARA, preferably between 1 and 10 BARA.

The contact time of the reactants with the catalyst is preferably between 1 and 60 seconds and advantageously between 5 and 25 seconds.

It has been found that recycling of the by-products of the oxychlorination reaction to the reactor leads to a reduction in the wastage of feedstock. In a preferred aspect of the present process, it is in fact possible to reduce feedstock wastage to zero, except for that portion which is lost in the form of combustion products and that lost in purge streams. This is due to the fact that the chlorinated hydrocarbon by-products of the oxychlorination reaction may be converted to VCM on further processing.

The chlorinated by-products formed during the oxychlorination of ethane to VCM are conveniently categorised as saturates, unsaturates and combustion products.

Saturates include ethyl chloride, 1,1 dichloroethane, 1,2 dichloroethane and 1,1,2 trichloroethane. Combustion products include carbon tetrachloride, chloroform and dichloromethane. Unsaturates include 1,1 dichloroethylene, cis 1,2 dichloroethylene, trans 1,2 dichloroethylene, trichloroethylene and perchloroethylene.

It is thought possible to recycle the chlorinated hydrocarbon by-products directly to the oxychlorination reaction. Although this would achieve some partial success, the total conversion of by-products to VCM would be low.

This is because the reactions which occur in the oxychlorination reaction are unable to convert unsaturated chlorinated hydrocarbons to VCM. Furthermore, many saturated chlorinated hydrocarbons will be converted to unsaturated chlorinated hydrocarbons by dehydrochlorination, and will therefore not be available for conversion to VCM.

Preferably, therefore, unsaturated chlorinated hydrocarbons are converted to saturated forms by a hydrogenation step.

Saturated chlorinated hydrocarbons are converted by dehydrochlorination and, if necessary, additional hydrogenation reactions into unsaturated hydrocarbons and eventually into VCM. FIG. 1 shows the reactions which occur in the oxychlorination and hydrogenation reactors used in the present invention.

By recycling the unsaturated by-products through a hydrogenation step, all of the chlorinated hydrocarbon by-products of the oxychlorination reaction may be recovered and their feedstock value is not wasted.

In the hydrogenation step, a feed of chlorinated by-products is brought together with hydrogen over a catalyst bed at elevated temperature and pressure. Suitable catalysts include platinum, palladium and rhodium, preferably operated at between 20° and 250° C., advantageously between 50° and 150° C., in a trickle bed reactor. Preferably, a large excess of hydrogen is used. However, any suitable catalyst known in the art is envisaged for use in the process of the invention, under appropriate operating conditions.

The unsaturated chlorinated hydrocarbons may be fed to the hydrogenation reactor in an essentially pure feed. However, in a preferred embodiment of the invention, they are supplied in an unpurified form together with saturated chlorinated hydrocarbon by-products and combustion products from the oxychlorination reactor. This eliminates the necessity for a separation stage to separate saturated from non-saturated by-products and combustion products.

The saturates are largely unaffected by this treatment, although under certain conditions they may undergo some hydro-dechlorination leading to the production of ethane. Combustion products will also undergo hydro-dechlorination, to yield methane and HCl.

Preferably, the components of the by-product feed will comprise these given below, within the mole fraction ratios given:

|  | MINIMUM | MAXIMUM |
|---|---|---|
| 1,1 dichloroethylene, | 0 | 10 |
| cis 1,3 dichloroethylene, | 0 | 10 |
| trans 1,3 dichloroethylene, | 0 | 20 |
| trichloroethylene, | 0 | 10 |
| perchloroethylene, | 0 | 10 |
| ethyl chloride, | 0 | 20 |
| 1,1 dichloroethane, | 0 | 10 |
| 1,2 dichloroethane, | 0 | 90 |
| 1,1,2 trichloroethane | 0 | 30 |
| carbon tetrachloride | 0 | 20 |
| chloroform | 0 | 20 |
| dichloromethane | 0 | 10 |
| sym-tetrachloroethane | 0 | 5 |

The reactor feed can also contain relatively small amounts of other materials such as chlorinated butanes, chlorinated butadienes and other chlorinated materials as well as hydrocarbons such as ethane and ethylene.

The invention is described, for the purposes of illustration only, in the following examples, with reference to FIG. 1, which is a schematic representation of reactions occurring in oxychlorination and hydrogenation reactors.

Examples 1 and 2

A catalyst was prepared containing 1.3% copper and 3.4% potassium by evaporation of an aqueous solution of the metal chlorides onto an alumina carrier. To a 250 cm$^3$ sample of de-ionised water was added 20 g of $CuCl_2.2H_2O$ and 35 g of KCl. The resultant solution was added stepwise to 500 g of catalyst carrier (Type SAHT-99, Production Chemicals Ltd.). This catalyst paste was dried by heating to 120° C. for 24 hours and then sieved to break up agglomerates before use. When prepared, the catalyst was found to have a surface area of 1 m$^2$/g and to have a mean particle size of 90 microns.

A catalyst charge of 400 cm$^3$ was loaded into a 50.8 mm diameter Inconel fluidised bed reactor to give a bed length of approximately 40 cm. The conversions and selectivity of the catalyst was measured using an on-line gas chromatograph. The reactor was heated electrically to the desired operating temperature and fed with a gas mixture of ethane, chlorine, nitrogen and oxygen and gave results as detailed in Table 1 example 1. The experiment was then repeated except that hydrogen chloride was substituted for chlorine and a higher flow of oxygen was used to account for increased stoichiometric requirement for oxygen—the results are shown as example 2, table 1. The use of hydrogen chloride instead of chorine resulted in a higher burning rate and a lower ethane conversion rate at a slightly lower oxygen conversion rate.

TABLE 1

|  |  | EXAMPLE 1 | EXAMPLE 2 |
|---|---|---|---|
| CONDITIONS | TEMP. (°C.) | 478.0 | 480.7 |
|  | PRESS. (BARG) | 0.1 | 0.1 |
| REACTANT FLOWS IN (LITERS PER HOUR) | $Cl_2$ | 21.1 | 0 |
|  | HCl | 0.0 | 48.0 |
|  | $C_2H_6$ | 37.5 | 37.5 |
|  | $N_2$ | 42.0 | 18.0 |
|  | $O_2$ | 30.0 | 42.0 |
| PRODUCT FLOWS OUT (LITERS PER HOUR) | $O_2$ | 1.6 | 2.9 |
|  | $N_2$ | 42.0 | 18.0 |
|  | CO | 0.2 | 0.9 |
|  | $CO_2$ | 4.0 | 4.6 |
|  | $C_2H_4$ | 5.8 | 5.0 |
|  | $C_2H_6$ | 2.0 | 3.8 |
|  | $C_2H_3Cl$ | 11.4 | 10.1 |
|  | $C_2H_5Cl$ | 4.9 | 4.7 |
|  | $C_2H_2Cl_2$ (A) | 2.8 | 3.3 |
|  | $C_2H_4Cl_2$ (B) | 0.6 | 0.6 |
|  | $C_2H_4Cl_2$ (C) | 4.5 | 3.4 |
|  | $C_2HCl_3$ | 0.2 | 0.3 |
|  | $C_2Cl_4$ | 2.0 | 2.0 |
|  | $C_2H_3Cl_3$ (D) | 0.2 | 0.2 |
|  | UNKOWNS | 0.1 | 0.1 |
|  | $CHCl_3$ | 0.2 | 0.3 |
|  | $CCl_4$ | 0.5 | 0.9 |
| CONVERSION % | $O_2$ | 94.5 | 93.2 |
|  | $C_2H_6$ | 94.8 | 89.9 |
| YIELD ON ETHANE REACTED | $C_2H_3Cl$ | 32.2 | 30.0 |
|  | $C_2H_5Cl$ | 13.9 | 13.8 |
|  | $C_2H_4$ | 16.3 | 14.8 |
|  | $C_2H_2Cl_2$ (A) | 7.9 | 9.9 |
|  | $C_2H_3Cl_3$ (D) | 0.5 | 0.5 |
|  | $C_2HCl_3$ | 0.6 | 0.9 |
|  | $C_2Cl_4$ | 5.9 | 8.4 |
|  | $C_2H_4Cl_2$ | 14.5 | 12.0 |
|  | $CO + CO_2$ | 5.9 | 8.4 |
|  | CT (SEC) | 4.6 | 4.1 |
|  | SLV (CM/SEC) | 4.4 | 5.0 |

(NOTES: A—All 3 isomers, B—1,1 isomer, C—1,2 isomer, D—1,1,2 isomer)

Examples 3 to 5

A further charge of the catalyst detailed above was prepared and a sample of a copper, potassium and cerium catalyst was also prepared. This was carried out in the same manner except cerium chloride was added to give a metal content of 0.74% by weight. The Cu/K catalyst was fed with a mixture of ethane, hydrogen chloride, oxygen and nitrogen. This experiment was then repeated except that the Cu/K/Ce catalyst was used. Both these sets of results are shown as example 3, table 2. This comparison of the conversion and selectivities of these two catalyst formulations was repeated under two further sets of conditions at different feedstock ratios (shown as examples 4 and 5, table 2). Under all three sets of conditions, the incorporation of cerium into the catalyst formulations results in a significant beneficial effect: the burning rate is reduced and the conversion rate of ethane is raised.

TABLE 2

|  |  | EXAMPLE 3 | | EXAMPLE 4 | | EXAMPLE 5 | |
|---|---|---|---|---|---|---|---|
|  |  | Cu/K | Cu/K/Ce | Cu/K | Cu/K/Ce | Cu/K | Cu/K/Ce |
| CONDITIONS | TEMP. (°C.) | 470.6 | 466.6 | 473.5 | 472.7 | 477.2 | 477.4 |
|  | PRESS. (BARG) | 0.03 | 0.04 | 0.03 | 0.05 | 0.03 | 0.06 |
| REACTANT | $Cl_2$ | 0 | 0 | 0 | 0 | 0 | 0 |
| FLOW IN | HCl | 60 | 60 | 60 | 60 | 60 | 60 |
| (LITERS PER | $C_2H_4$ | 30 | 30 | 30 | 30 | 48 | 48 |
| HOUR) | $N_2$ | 21.7 | 22 | 21.7 | 22 | 5.8 | 0 |
|  | $O_2$ | 30 | 30 | 46 | 46 | 48 | 48 |
| PRODUCT | $O_2$ | 1.3 | 0.6 | 5.1 | 2.6 | 1.5 | 1.2 |
| FLOWS OUT | $N_2$ | 21.7 | 22.0 | 21.7 | 22.0 | 5.8 | 0.0 |
| (LITERS PER | CO | 0.8 | 0.7 | 1.4 | 0.4 | 1.6 | 0.0 |
| HOUR) | $CO_2$ | 1.8 | 0.9 | 3.7 | 3.4 | 4.2 | 3.8 |
|  | $C_2H_4$ | 3.9 | 4.4 | 1.7 | 1.0 | 8.4 | 9.0 |
|  | $C_2H_6$ | 3.2 | 1.6 | 1.5 | 0.7 | 5.4 | 3.6 |
|  | $C_2H_3Cl$ | 7.7 | 8.6 | 4.8 | 4.7 | 12.4 | 13.6 |
|  | $C_2H_5Cl$ | 3.6 | 3.2 | 2.5 | 1.6 | 5.8 | 6.2 |
|  | $C_2H_2Cl_2$ (A) | 2.6 | 3.3 | 6.8 | 10.4 | 2.9 | 3.2 |
|  | $C_2H_4Cl_2$ (B) | 0.5 | 0.5 | 0.6 | 0.3 | 0.6 | 0.7 |
|  | $C_2H_4Cl_2$ (C) | 2.4 | 4.2 | 1.4 | 1.7 | 4.2 | 6.7 |
|  | $C_2HCl_3$ | 0.2 | 0.4 | 1.7 | 2.3 | 0.3 | 0.2 |
|  | $C_2Cl_4$ | 1.5 | 0.0 | 2.6 | 0.1 | 1.4 | 0.1 |
|  | $C_2H_3Cl_3$ (D) | 0.0 | 2.4 | 0.1 | 4.5 | 0.2 | 2.4 |
|  | UNKOWNS | 0.0 | 0.2 | 0.1 | 0.3 | 0.2 | 0.2 |
|  | $CHCl_3$ | 0.2 | 0.2 | 0.4 | 0.4 | 0.5 | 0.4 |
|  | $CCl_4$ | 0.7 | 0.4 | 1.4 | 1.2 | 1.0 | 0.9 |
| CONVERSION | $O_2$ | 95.6 | 98.1 | 89.0 | 94.4 | 96.8 | 97.6 |
| % | $C_2H_6$ | 89.3 | 94.8 | 95.1 | 97.8 | 88.8 | 92.6 |
| YIELD ON | $C_2H_3Cl$ | 28.8 | 30.3 | 17.0 | 16.1 | 29.0 | 30.7 |
| ETHANE | $C_2H_5Cl$ | 13.4 | 11.1 | 8.9 | 5.4 | 13.7 | 13.9 |
| REACTED | $C_2H_4$ | 14.6 | 15.5 | 5.8 | 3.4 | 19.7 | 20.4 |
|  | $C_2H_2Cl_2$ (A) | 10.9 | 11.8 | 26.5 | 35.9 | 7.3 | 7.3 |
|  | $C_2H_3Cl_3$ (D) | 0.1 | 8.7 | 0.5 | 15.7 | 0.5 | 5.5 |
|  | $C_2HCl_3$ | 0.8 | 1.6 | 6.5 | 7.9 | 0.6 | 0.4 |
|  | $C_2Cl_4$ | 6.0 | 0.1 | 10.1 | 0.4 | 3.4 | 0.2 |
|  | $C_2H_4Cl_2$ | 12.0 | 16.9 | 7.7 | 7.2 | 12.0 | 16.7 |
|  | $CO + CO_2$ | 5.3 | 2.9 | 9.8 | 6.6 | 7.2 | 4.3 |
|  | CT (SEC) | 4.1 | 4.2 | 3.7 | 3.8 | 3.6 | 3.8 |
|  | SLV (CM/SEC) | 5.0 | 4.9 | 5.5 | 5.4 | 5.7 | 5.4 |

(NOTES: A-All 3 isomers, B-1, 1 isomer, C - 1, 2 isomer, D -1, 1, 2 isomer)

Examples 6 to 22

Using Cu/K/Ce catalyst formulated in the same manner as detailed in example 2, the reactor was fed with a mixture of ethane, oxygen, 1,2 dichloroethane and nitrogen. Table 3 presents the results of a series of experiments under different temperatures and feedstock ratios. A range of conversions of ethane and oxygen are evident in the results as well as a range of reaction selectivities. The most attractive results are achieved at high temperature using a low flow of oxygen (example 13).

Examples 23 to 25

Again using the Cu/K/Ce formulation detailed in example 2, the reactor was fed with a mixture of ethane, oxygen, 1,2 dichloroethane, ethyl chloride and nitrogen: the results are shown as example 23, table 4. The experiment was then repeated but this time the reactor contained half the usual charge of catalyst and half of bare catalyst support. The catalyst was fluidised with nitrogen and held at 470° C. for 8 hours before being fed with a mixture of ethane, oxygen, 1,2 dichloroethane, ethyl chloride and nitrogen and the results produced are displayed as example 24, table 4. The procedure was repeated again except using a catalyst that contained only 25% of the original charge of catalyst together with 75% of bare support. Results from this experiment are shown as example 25, table 4.

The results form this series show that the effect on feedstock conversion and selectivity is only measurable at between 50% and 25% of the initial metal concentration on the catalyst.

TABLE 3

|  | Example | 6 | 7 | 8 | 9 | 10 | 11 | 12 |
|---|---|---|---|---|---|---|---|---|
| CONDITIONS | TEMP. (°C.) | 490 | 540 | 453 | 449 | 451 | 511 | 524 |
|  | PRESS. (BARG) | 0.83 | 0.86 | 0.76 | 0.75 | 0.78 | 0.83 | 0.87 |
| FLOWS IN | $C_2H_6$ | 29.90 | 29.9 | 30.4 | 30.3 | 50.7 | 30.2 | 51 |
| (LITERS PER | $N_2$ | 143.6 | 143.5 | 143.5 | 143.5 | 143.7 | 142.3 | 142.3 |
| HOUR) | $C_2H_4Cl_2$ (D) | 40 | 40 | 40 | 40 | 40 | 40 | 40.0 |
|  | $O_2$ | 50.7 | 50.8 | 50.4 | 30.5 | 30.4 | 30.5 | 50.5 |
| FLOWS OUT | $O_2$ | 5.9 | 4.55 | 13.16 | 6.70 | 4.61 | 2.48 | 2.25 |

TABLE 3-continued

| | | | | | | | | |
|---|---|---|---|---|---|---|---|---|
| (LITERS PER HOUR) | $N_2$ | 143.6 | 143.5 | 143.5 | 143.5 | 143.7 | 142.3 | 142.3 |
| | CO | 1.11 | 4.70 | 0.71 | 0.62 | 0.43 | 3.87 | 6.01 |
| | $CO_2$ | 15.85 | 14.25 | 13.32 | 8.61 | 9.94 | 4.71 | 16.61 |
| | $C_2H_4$ | 7.47 | 10.31 | 8.33 | 4.11 | 5.24 | 15.19 | 24.55 |
| | $C_2H_6$ | 3.76 | 3.47 | 6.64 | 13.04 | 28.83 | 5.24 | 14.70 |
| | $C_2H_3Cl$ | 21.42 | 23.17 | 10.75 | 9.42 | 7.25 | 28.62 | 22.74 |
| | $C_2H_5Cl$ | 3.67 | 2.09 | 7.43 | 8.62 | 10.99 | 2.37 | 3.61 |
| | $C_2H_2Cl_2$ (A) | 4.52 | 4.61 | 0.94 | 0.50 | 0.23 | 2.54 | 0.98 |
| | $C_2H_4Cl_2$ (B) | 0.29 | 0.23 | 0.48 | 0.38 | 0.27 | 0.17 | 0.10 |
| | $C_2H_4Cl_2$ (C) | 20.09 | 11.05 | 30.10 | 32.49 | 35.18 | 15.48 | 15.21 |
| | $C_2HCl_3$ | 0.67 | 1.17 | 0.15 | 0.02 | 0.00 | 1.11 | 0.94 |
| | $C_2Cl_4$ | 0.54 | 1.12 | 1.07 | 0.62 | 0.28 | 0.44 | 0.11 |
| | $C_2H_3Cl_3$ (D) | 2.33 | 0.76 | 0.30 | 0.19 | 0.00 | 0.58 | 0.21 |
| | Unkowns | 0.13 | 0.71 | 0.12 | 0.09 | 0.28 | 0.73 | 0.56 |
| | $CHCl_3$ | 0.25 | 0.14 | 0.21 | 0.17 | 0.11 | 0.09 | 0.00 |
| | $CCl_4$ | 0.30 | 0.29 | 0.17 | 0.18 | 0.12 | 0.23 | 0.00 |
| CONV. % | $O_2$ | 88.37 | 91.05 | 73.88 | 78.03 | 84.83 | 91.88 | 95.54 |
| | $C_2H_6$ | 87.44 | 88.41 | 78.15 | 56.96 | 43.14 | 82.66 | 71.17 |
| YIELD | $CO + CO_2$ | 32.43 | 35.86 | 29.51 | 26.72 | 23.72 | 17.18 | 31.16 |
| | CT SECS | 3.85 | 3.74 | 3.85 | 4.17 | 3.90 | 4.05 | 3.49 |
| | SLV CM/S | 5.30 | 5.45 | 5.29 | 4.89 | 5.22 | 5.03 | 5.84 |

| | Example | 13 | 14 | 15 | 16 | 17 | 18 | 19 |
|---|---|---|---|---|---|---|---|---|
| CONDITIONS | TEMP. (°C.) | 510 | 514 | 453 | 457 | 518 | 518 | 491 |
| | PRESS. (BARG) | 0.76 | 0.83 | 0.73 | 0.75 | 0.76 | 0.77 | 0.79 |
| FLOWS IN | $C_2H_6$ | 50.8 | 30.3 | 30.2 | 50.8 | 30.7 | 49.6 | 40.2 |
| (LITERS PER | $N_2$ | 101.8 | 143.7 | 144.9 | 107.8 | 103.7 | 82.1 | 122.2 |
| HOUR) | $C_2H_4Cl_2$ (D) | 60.0 | 40.0 | 44.07 | 69.86 | 69.98 | 69.40 | 53.16 |
| | $O_2$ | 29.75 | 29.06 | 50.6 | 50.6 | 50.6 | 50.6 | 40.1 |
| FLOWS OUT | $O_2$ | 0.10 | 0.10 | 11.25 | 6.74 | 1.51 | 0.71 | 0.92 |
| (LITERS PER | $N_2$ | 101.8 | 143.7 | 144.9 | 107.8 | 103.7 | 82.1 | 122.2 |
| HOUR) | CO | 2.31 | 3.31 | 0.27 | 0.26 | 3.11 | 4.44 | 2.09 |
| | $CO_2$ | 3.80 | 7.58 | 13.20 | 13.98 | 7.98 | 11.09 | 8.48 |
| | $C_2H_4$ | 25.58 | 19.46 | 3.56 | 8.12 | 9.67 | 21.91 | 16.80 |
| | $C_2H_6$ | 18.20 | 7.93 | 9.84 | 17.81 | 3.24 | 10.98 | 7.86 |
| | $C_2H_3Cl$ | 37.70 | 21.84 | 11.32 | 17.51 | 40.66 | 40.28 | 31.99 |
| | $C_2H_5Cl$ | 3.37 | 1.71 | 7.65 | 13.72 | 1.95 | 3.41 | 4.24 |
| | $C_2H_2Cl_2$ (A) | 1.89 | 1.38 | 1.06 | 1.05 | 10.11 | 3.46 | 5.23 |
| | $C_2H_4Cl_2$ (B) | 0.13 | 0.05 | 0.55 | 0.69 | 0.12 | 0.23 | 0.19 |
| | $C_2H_4Cl_2$ (C) | 27.06 | 12.41 | 32.64 | 54.83 | 18.01 | 22.81 | 22.76 |
| | $C_2HCl_3$ | 1.11 | 0.81 | 0.10 | 0.11 | 3.33 | 2.30 | 0.98 |
| | $C_2Cl_4$ | 0.25 | 0.14 | 1.48 | 1.44 | 1.41 | 0.40 | 1.26 |
| | $C_2H_3Cl_3$ (D) | 0.38 | 0.00 | 0.23 | 0.28 | 1.69 | 0.93 | 0.41 |
| | Unkowns | 0.54 | 0.54 | 0.02 | 0.26 | 1.56 | 1.13 | 0.67 |
| | $CHCl_3$ | 0.00 | 0.00 | 0.21 | 0.39 | 0.22 | 0.00 | 0.10 |
| | $CCl_4$ | 0.00 | 0.00 | 0.25 | 0.29 | 0.38 | 0.16 | 0.30 |
| CONV. % | $O_2$ | 99.66 | 99.66 | 77.78 | 86.68 | 97.01 | 98.60 | 97.70 |
| | $C_2H_6$ | 64.17 | 73.82 | 67.41 | 64.94 | 89.46 | 77.86 | 80.45 |
| YIELD | $CO + CO_2$ | 9.38 | 24.35 | 33.09 | 21.58 | 20.20 | 20.11 | 16.34 |
| | CT SECS | 3.91 | 4.03 | 3.71 | 3.61 | 3.67 | 3.74 | 3.86 |
| | SLV CM/S | 5.22 | 5.06 | 5.49 | 5.64 | 5.55 | 5.44 | 5.28 |

| | | Example | 20 | 21 | 22 |
|---|---|---|---|---|---|
| | CONDITIONS | TEMP. (°C.) | 531 | 520 | 470 |
| | | PRESS. (BARG) | 0.8 | 0.8 | 0.77 |
| | FLOWS IN | $C_2H_6$ | 50.4 | 50.2 | 44.9 |
| | (LITERS PER | $N_2$ | 102.49 | 102.3 | 102.6 |
| | HOUR) | $C_2H_4Cl_2$ (D) | 44.47 | 57.60 | 64.00 |
| | | $O_2$ | 50.1 | 30 | 35 |
| | FLOWS OUT | $O_2$ | 0.31 | 0.21 | 0.56 |
| | (LITERS PER | $N_2$ | 102.5 | 102.3 | 102.6 |
| | HOUR) | CO | 4.31 | 2.42 | 2.11 |
| | | $CO_2$ | 16.78 | 8.00 | 10.13 |
| | | $C_2H_4$ | 23.30 | 21.69 | 14.52 |
| | | $C_2H_6$ | 16.10 | 23.73 | 17.58 |
| | | $C_2H_3Cl$ | 23.32 | 24.46 | 21.29 |
| | | $C_2H_5Cl$ | 2.34 | 2.31 | 5.62 |
| | | $C_2H_2Cl_2$ (A) | 1.56 | 2.14 | 3.19 |
| | | $C_2H_4Cl_2$ (B) | 0.08 | 0.04 | 0.24 |
| | | $C_2H_4Cl_2$ (C) | 9.65 | 20.77 | 35.46 |
| | | $C_2HCl_3$ | 1.11 | 0.89 | 0.44 |
| | | $C_2Cl_4$ | 0.15 | 0.15 | 0.60 |
| | | $C_2H_3Cl_3$ (D) | 0.57 | 0.33 | 0.00 |
| | | Unkowns | 0.48 | 0.18 | 0.71 |
| | | $CHCl_3$ | 0.00 | 0.00 | 0.00 |
| | | $CCl_4$ | 0.00 | 0.00 | 0.14 |
| | CONV. % | $O_2$ | 99.39 | 99.32 | 98.41 |

TABLE 3-continued

|  |  | | | |
|---|---|---|---|---|
|  | YIELD | $C_2H_6$ | 68.06 | 52.73 | 60.85 |
|  |  | $CO + CO_2$ | 30.74 | 19.68 | 22.39 |
|  |  | CT SECS | 3.82 | 4.00 | 4.09 |
|  |  | SLV CM/S | 5.33 | 5.09 | 4.98 |

(NOTES: A—All 3 isomers, B-1, 1 isomer, C - 1, 2 isomer, D -1, 1, 2 isomer)

TABLE 4

|  |  | EXAMPLE 23 | EXAMPLE 24 | EXAMPLE 25 |
|---|---|---|---|---|
| CONDITIONS | TEMP. (°C.) | 490.10 | 491.4 | 490.1 |
|  | PRESS. (BARG) | 0.05 | 0.08 | 0.13 |
| REACTANT FLOWS IN (LITERS PER HOUR) | $C_2H_6$ | 35.30 | 35.43 | 35.40 |
|  | $N_2$ | 59.90 | 59.70 | 69.10 |
|  | $C_2H_4Cl_2$ (C) | 40.00 | 40.29 | 40.00 |
|  | $C_2H_5Cl$ | 8.82 | 8.78 | 12.24 |
|  | $O_2$ | 28.00 | 27.70 | 28.20 |
| PRODUCT FLOWS OUT (LITERS PER HOUR) | $O_2$ | 0.37 | 0.19 | 2.56 |
|  | CO | 0.29 | 1.07 | 1.47 |
|  | $CO_2$ | 2.24 | 1.96 | 2.58 |
|  | $C_2H_4$ | 18.35 | 17.32 | 18.55 |
|  | $C_2H_6$ | 8.21 | 8.07 | 9.20 |
|  | $C_2H_3Cl$ | 25.86 | 23.00 | 21.52 |
|  | $C_2H_5Cl$ | 8.58 | 9.15 | 11.78 |
|  | $C_2H_2Cl_2$ (A) | 1.48 | 1.09 | 0.95 |
|  | $C_2H_4Cl_2$ (B) | 0.35 | 0.46 | 0.59 |
|  | $C_2H_4Cl_2$ (C) | 19.47 | 21.71 | 23.86 |
|  | $C_2HCl_3$ | 0.27 | 0.21 | 0.13 |
|  | $C_2Cl_4$ | 0.35 | 0.21 | 0.14 |
|  | $C_2H_3Cl_3$ (D) | 0.86 | 0.80 | 0.67 |
|  | UNKOWNS | 0.18 | 0.00 | 0.10 |
|  | $CHCl_3$ | 0.12 | 0.15 | 0.24 |
|  | $CCl_4$ | 0.19 | 0.14 | 0.23 |
| CONVERSIONS % | $O_2$ | 98.70 | 99.31 | 90.92 |
|  | $C_2H_6$ | 76.73 | 77.21 | 74.00 |
| YIELD ON ETHANE REACTED | $C_2H_3Cl$ | 95.46 | 84.08 | 82.17 |
|  | $CO + CO_2$ | 4.68 | 5.55 | 7.74 |
|  | $C_2H_3Cl_3$ (D) | 3.17 | 2.93 | 2.37 |
|  | $C_2HCl_3$ | 0.99 | 0.78 | 0.49 |
|  | $C_2Cl_4$ | 1.29 | 0.76 | 0.53 |
|  | CT SECS | 3.28 | 3.47 | 3.38 |
|  | SLV CM/S | 6.21 | 5.87 | 6.03 |

(NOTES: A—All 3 isomers, B—1,1 isomer, C—1,2 isomer, D—1,1,2 isomer)

Example 26

A catalyst containing 1.3% copper and 3.4% potassium was prepared by evaporation of an aqueous solution of the metal chlorides onto an Alumina carrier. To a 250 $cm^3$ sample of de-ionised water was added 20 g of $CuCl_2.2H_2O$ and 35 g of KCl. The resultant solution was added stepwise to 500 g of catalyst carrier (Type SAHT-99, Production Chemicals Ltd.). This catalyst paste was dried by heating to 120° C. for 24 hours and then sieved to break up agglomerates before use. When prepared, the catalyst was found to have a surface area of 1 $m^2/g$ and to have a mean particle size of 90 microns.

A catalyst charge of 400 $cm^3$ was loaded into a 5.08 mm diameter Inconel fluidised bed reactor to give a bed length of approximately 40 cm. The conversions and selectivity achieved by the catalyst was measured using an on-line gas chromatograph. The reactor was heated electrically to the desired operating temperature and a reactor feed consisting of ethane, hydrogen chloride, nitrogen and oxygen was used. The feed details together with the results are shown as example 26, table 5.

Example 27

Using the same catalyst as example 26 the reactor was operated under the same conditions except with an increased hydrogen chloride flow and without a nitrogen flow. The results are displayed in table 5.

In example 27, the excess hydrogen chloride supplied was not able to take part in the oxychlorination reaction as all of the oxygen has been consumed at the lower hydrogen chloride flow rate shown in example 26. It is seen from the table that by increasing the flow of hydrogen chloride to the reactor, the yield to burning products (mainly $CO_2$) decreases from 8.44 to 7.27% of the ethane reacted.

TABLE 5

|  |  | EXAMPLE 26 | EXAMPLE 27 |
|---|---|---|---|
| CONDITIONS | TEMP. (°C.) - A | 480.7 | 477.5 |
|  | PRESS (BARG) | 0.1 | 0.1 |
| REACTANT FLOWS IN (LITERS PER HOUR) | HCl | 48.0 | 66.0 |
|  | $C_2H_6$ | 37.5 | 37.5 |
|  | $N_2$ | 18.0 | 0.0 |
|  | $O_2$ | 42.0 | 43.2 |
| PRODUCT FLOWS OUT (LITERS PER HOUR) | $O_2$ | 2.9 | 2.9 |
|  | CO | 0.9 | 1.4 |
|  | $CO_2$ | 4.6 | 3.5 |
|  | $C_2H_4$ | 5.0 | 4.5 |
|  | $C_2H_3Cl$ | 10.1 | 10.0 |
|  | $C_2H_5Cl$ | 4.7 | 4.8 |
|  | $C_2H_2Cl_2$ (A) | 3.3 | 4.4 |
|  | $C_2H_4Cl_2$ (B) | 0.6 | 0.7 |
|  | $C_2H_4Cl_2$ (C) | 3.4 | 3.3 |
|  | $C_2HCl_3$ | 0.3 | 0.3 |
|  | $C_2Cl_4$ | 2.0 | 2.4 |
|  | $C_2H_3Cl_3$ (D) | 0.2 | 0.1 |
|  | UNKNOWNS | 0.1 | 0.1 |
|  | $CHCl_3$ | 0.3 | 0.4 |
|  | $CCl_4$ | 0.9 | 1.1 |
| CONVERSION % | $O_2$ | 93.2 | 93.3 |
|  | $C_2H_6$ | 89.9 | 88.8 |
| YIELD ON ETHANE REACTED | $C_2H_3Cl$ | 30.0 | 30.1 |
|  | $C_2H_5Cl$ | 13.8 | 14.4 |
|  | $C_2H_4$ | 14.8 | 13.5 |
|  | $C_2H_2Cl_2$ (A) | 9.9 | 13.0 |
|  | $C_2H_3Cl_3$ (D) | 0.5 | 0.3 |
|  | $C_2HCl_3$ | 0.9 | 1.0 |
|  | $C_2Cl_4$ | 8.4 | 7.3 |
|  | $C_2H_4Cl_2$ | 12.0 | 11.7 |
|  | $CO + CO_2$ | 8.4 | 7.3 |
|  | CT (SEC) | 4.1 | 4.1 |
|  | SLV (CM/SEC) | 5.0 | 5.0 |

(NOTES: A—All 3 isomers, B—1,1 isomer, C—1,2 isomer, D—1,1,2 isomer)

Example 28

Using a catalyst of the same composition as that in example 26 and utilising a mixed chlorohydrocarbon feed, the effect of increasing the hydrogen chloride flow is shown as example 28A to 28C, table 6.

Example 29

Again using catalyst of the same composition as in example 20 and utilising a mixed chlorohydrocarbon feed, the effect of increasing the hydrogen chloride flow but at a higher temperature than example 28 is shown as example 29A to 29C, table 6.

Example 30

Again using catalyst of the same composition as in example 20 and utilising a mixed chlorohydrocarbon feed, the effect of increasing the hydrogen chloride flow but at a higher temperature than example 28 and a lower oxygen flow is shown as example 30A to 30C, table 6.

Table 6 shows that under the three combinations of temperature and oxygen flow used, an increasing hydrogen chloride flow results in a decrease in the ethane burning rate. Furthermore, the efficiency with which ethane is converted within the reactor also increases as the hydrogen chloride flow to the reactor is increased.

Example 31

Into a fluidised bed reactor are fed the following components:

| Feeds | |
|---|---|
| Ethane | 1.0 |
| Oxygen | 0.85 |

| Direct chlorination product | |
|---|---|
| EDC | 0.35 (0.35 chlorine feed) |
| Carbon oxides | 1.1 |
| Hydrogenation recycle | |
| Ethyl chloride | 0.37 |
| EDC | 0.78 |
| 1,1 dichloroethane | 0.02 |
| 1,1,2-trichloroethane | 0.04 |
| Sym-tetrachloroethane | 0.01 |
| Carbon tetrachloride | 0.03 |
| Hydrogen chloride recycle | |
| HCl | 0.1 |

The above molar proportions represent the steady state operating flows into the reactor for the process. Chlorine enters the process as elemental chlorine fed to the direct chlorination reactor.

Ethane is mixed with the HCl recycle and fed to the reactor below the catalyst support plate. In the windbox it mixes with the vaporised hydrogenation recycle and the direct chlorination products. The combined streams are at a temperature of 150° C. and a pressure of 5.5 bara.

The mixture passes through the support grid to fluidise the catalyst which operates at a temperature of 450° C. The oxygen feed is added via a gas sparger which is situated just above the support grid. The residence time is 12 seconds and the reaction temperature is maintained steady by removing reaction heat by heat transfer coils immersed in the bed and cooled by circulating hot salt. The product spectrum, on the same basis as the feed given above, is:

| Products | |
|---|---|
| Ethane | 0.24 |
| Ethylene | 0.35 |
| VCM | 0.70 |
| Oxygen | 0.08 |

TABLE 6

| | | EXAMPLE 28 | | | EXAMPLE 29 | | | EXAMPLE 30 | | |
|---|---|---|---|---|---|---|---|---|---|---|
| | | A | B | C | A | B | C | A | B | C |
| CONDITIONS | TEMP. (°C.) | 462 | 463 | 464 | 491 | 491 | 491 | 490 | 491 | 490 |
| | PRESS (BARG) | 0.05 | 0.06 | 0.06 | 0.07 | 0.07 | 0.08 | 0.05 | 0.05 | 0.06 |
| REACTANT | $C_2H_6$ | 35.3 | 35.3 | 35.3 | 35.53 | 35.60 | 35.57 | 35.3 | 35.3 | 35.3 |
| FLOW IN | HCl | 0 | 5 | 10 | 0 | 5 | 10 | 0 | 5 | 10 |
| (LITERS PER | $N_2$ | 59.2 | 59.1 | 59.1 | 59.6 | 59.6 | 59.6 | 59.9 | 59.9 | 59.9 |
| HOUR) | $C_2H_4Cl_2$ (C) | 47.6 | 47.6 | 47.6 | 37.5 | 37.5 | 37.5 | 40.0 | 40.0 | 40.0 |
| | $C_2H_3Cl$ | 17.5 | 16.4 | 16.4 | 7.1 | 7.1 | 7.1 | 8.8 | 8.8 | 8.8 |
| | $O_2$ | 37.8 | 37.8 | 37.8 | 38.2 | 38.2 | 38.2 | 28 | 28 | 28 |
| PRODUCT | CO | 0.0 | 0.0 | 0.0 | 0.0 | 0.2 | 0.2 | 0.3 | 0.3 | 0.3 |
| FLOWS OUT | $CO_2$ | 8.3 | 6.5 | 5.3 | 7.3 | 5.5 | 4.1 | 2.2 | 1.8 | 1.5 |
| (LITERS PER | $C_2H_4$ | 15.6 | 13.8 | 13.7 | 15.7 | 15.2 | 14.5 | 18.3 | 17.9 | 17.3 |
| HOUR) | $C_2H_3Cl$ | 18.6 | 19.6 | 21.1 | 24.3 | 26.3 | 27.8 | 25.9 | 26.7 | 26.9 |
| | $C_2H_4Cl$ | 17.3 | 16.7 | 15.8 | 7.3 | 6.7 | 6.4 | 8.6 | 8.4 | 8.5 |
| | $C_2H_2Cl_2$ (A) | 1.3 | 1.6 | 2.2 | 2.1 | 2.9 | 3.8 | 1.5 | 1.6 | 1.8 |
| | $C_2H_4Cl_2$ (B) | 0.6 | 0.7 | 0.7 | 0.4 | 0.4 | 0.4 | 0.4 | 0.4 | 0.4 |
| | $C_2H_4Cl_2$ (C) | 31.6 | 32.5 | 32.2 | 17.0 | 16.5 | 16.3 | 19.5 | 19.2 | 19.2 |
| | $C_2HCl_3$ | 0.1 | 0.1 | 0.1 | 0.2 | 0.3 | 0.3 | 0.3 | 0.3 | 0.2 |
| | $C_2Cl_4$ | 0.2 | 0.2 | 0.1 | 0.5 | 0.0 | 0.3 | 0.3 | 0.3 | 0.2 |
| | $C_2H_3Cl_3$ (D) | 1.6 | 2.3 | 2.9 | 1.2 | 1.6 | 1.3 | 0.9 | 0.9 | 0.6 |
| | UNKNOWNS | 0.1 | 0.1 | 0.1 | 0.0 | 0.0 | 0.1 | 0.2 | 0.1 | 0.1 |
| | $CHCl_3$ | 0.2 | 0.2 | 0.2 | 0.2 | 0.2 | 0.1 | 0.1 | 0.1 | 0.1 |
| | $CCl_4$ | 0.3 | 0.4 | 0.4 | 0.3 | 0.3 | 0.2 | 0.2 | 0.2 | 0.2 |
| CONVERSIONS | $O_2$ | 89.9 | 91.7 | 92.7 | 96.2 | 96.9 | 95.7 | 98.7 | 98.9 | 98.4 |
| % | $C_2H_6$ | 66.8 | 70.3 | 73.3 | 82.9 | 85.6 | 86.6 | 76.7 | 77.4 | 78.8 |
| YIELD ON | $C_2H_3Cl$ | 78.8 | 78.9 | 81.4 | 82.4 | 86.4 | 90.4 | 95.5 | 97.8 | 96.8 |
| ETHANE | $CO + CO_2$ | 17.6 | 13.0 | 10.3 | 12.4 | 9.3 | 7.0 | 4.7 | 3.9 | 3.1 |
| REACTED | $C_2H_3Cl_3$ (D) | 6.7 | 9.2 | 11.1 | 4.1 | 5.2 | 4.1 | 3.2 | 3.2 | 2.3 |
| | $C_2HCl_3$ | 0.4 | 0.4 | 0.5 | 0.8 | 1.1 | 1.1 | 1.0 | 1.1 | 0.9 |
| | $C_2Cl_4$ | 0.7 | 0.6 | 0.5 | 1.6 | 0.0 | 0.9 | 1.3 | 1.2 | 0.8 |
| | CT SECS | 3.1 | 3.0 | 2.9 | 3.3 | 3.3 | 3.3 | 3.3 | 3.3 | 3.3 |
| | SLV CM/S | 6.6 | 6.7 | 6.9 | 6.1 | 6.1 | 6.1 | 6.2 | 6.2 | 6.2 |

(NOTES: A-All 3 isomers, B-1, 1 isomer, C - 1, 2 isomer, D -1, 1, 2 isomer)

-continued

| Products | |
|---|---|
| EDC | 0.35 |
| Carbon oxides | 1.24 |
| Ethyl chloride | 0.37 |
| EDC | 0.78 |
| Dichloroethylenes | 0.05 |
| Trichloroethylene | 0.01 |
| 1,1,2-trichloroethane | 0.02 |
| Perchloroethylene | 0.01 |
| Carbon tetrachloride | 0.03 |
| HCl | 0.1 |
| Water | 1.31 |

We have found that as the HCl content of the gases coming out of the ethane oxychlorination reactor is allowed to fall to a very low level (almost complete reaction) then the amount of ethane which is converted to burning products rises steeply. By maintaining an excess of HCl the burning can be reduced from 20% (no HCl in the off gases) to 3% (10% HCl in the off gas). We have also found that it is possible to reduce the operating temperature of the reactor to 450° C., whilst still maintaining acceptable feed conversion and selectivity, by increasing the residence time of the reactants from 2 seconds to 12 seconds. This feature is important because known fabrication metals suffer greatly enhanced corrosion/erosion above 470° C.

The reaction mixture, given above, is separated into a water stream, an anhydrous HCl stream, a dry lights stream (all components lighter than VCM), a pure VCM stream and a heavy by-products stream.

Water is removed from the reactor products by first performing a partial condensation which gives an aqueous HCl phase, a wet liquid organic phase and a wet vapour phase. The aqueous phase is mixed with a calcium chloride solution and then distilled to produce a top product of anhydrous HCl which is recycled to the reactor. The base product is taken off as a side stream vapour which is condensed to give an uncontaminated water stream. The calcium chloride stream is recycled to the column feed. The wet liquid phase is azeotropically dried in a distillation column. The wet top product is recycled back to the phase separation section whilst the dry base product is pumped forward for distillative separation. The wet vapour is dried by contacting it countercurrently with 20% w/w HCl solution cooled to −20° C. A purge is taken from this stream to the calcium chloride column in order to preserve the materials balance. The dry vapour is then compressed and transferred to the distillation section.

Compressed vapour products and the dried liquid organic stream are fed together to a distillation column (lights column) which operates with ethane as the light key and VCM as the heavy key. After heat interchange with the column feed the vapour product is reacted with chlorine to produce EDC from the ethylene component of the feed. This can be done in a vapour phase fluid bed, a fixed bed or in a conventional liquid phase reactor.

A fluidised bed vapour phase direct chlorinator is preferred for this reaction as the heat of reaction can be recovered as steam and there is no product contamination, due to iron for example, to impact on the environment. The reactor operates at 6 bara and 200° C. The off gas is recycled to the oxychlorination reactor but a small purge is taken from the stream to keep the carbon oxides in balance. EDC is removed from the purge stream using carbon bed adsorption. The lean gas is incinerated.

The base flow from the lights column is distilled (VCM column) to remove VCM as top product. The base product is reacted with hydrogen in a trickle bed reactor. In this reactor any olefinic species (e.g. dichloroethylenes, trichloroethylene and perchloroethylene) are converted to their saturated counterparts. The reaction takes place adiabatically at 10 bara and 75° C. with a tenfold hydrogen excess. The saturated stream is then vaporised and recycled to the oxychlorination reactor where the saturates dehydrochlorinate. By this mechanism all compounds, other than carbon tetrachloride, eventually convert to VCM.

We claim:

1. A method for the catalytic oxychlorination of ethane to VCM comprising combining ethane and a chlorine source in an oxychlorination reactor in the presence of an oxychlorination catalyst, the reaction conditions being selected so as to maintain an excess of HCl, separating the VCM product from the output of the reactor and recycling the by-products to the reactor.

2. A method according to claim 1 wherein the catalyst comprises a copper salt and an alkali metal salt deposited on an inert support.

3. A method according to claim 2 wherein the catalyst further comprises a lanthanide salt.

4. A method according to claim 3 wherein the catalyst contains copper, potassium and cerium in the weight percentages 1.3%:3.4%:0.74%.

5. A method according to claim 2 wherein the metal salts are metal chlorides.

6. A method according to any one preceding claim which is operable between the temperatures of 400° and 550° C.

7. A method according to claim 6 which is operable at between 450° and 470° C.

8. A method according to claim 1 wherein the recycled by-products are subjected to a hydrogenation step before entering the oxychlorination reactor.

9. A method according to claim 8 wherein only unsaturated chlorinated by-products are subjected to the hydrogenation step.

10. A method according to claim 8 or claim 9, wherein the hydrogenation step takes place in a hydrogenation reactor in the presence of a catalyst containing platinum, palladium or rhodium, at a temperature between 20° and 250° C.

11. A method according to claim 1 wherein the vapor by-products are reacted with chlorine to produce ethylene dichloride.

* * * * *